United States Patent [19]

Matsuno et al.

[11] Patent Number: 4,533,781
[45] Date of Patent: Aug. 6, 1985

[54] PROCESS FOR PREPARING 4-METHYL-1-PENTENE

[75] Inventors: Mitsuo Matsuno, Kawasaki; Michio Kudoh; Hiroshuke Imai, both of Yokohama, all of Japan

[73] Assignee: Nippon Oil Company, Ltd., Japan

[21] Appl. No.: 665,307

[22] Filed: Oct. 26, 1984

[30] Foreign Application Priority Data

Oct. 29, 1983 [JP] Japan ................... 58-203508
Dec. 13, 1983 [JP] Japan ................... 58-233654
Apr. 11, 1984 [JP] Japan ................... 59-70915

[51] Int. Cl.$^3$ ................................ C07C 3/02
[52] U.S. Cl. ........................ 585/516; 585/530
[58] Field of Search ................. 585/516, 530

[56] References Cited

U.S. PATENT DOCUMENTS

| | | | |
|---|---|---|---|
| 3,291,752 | 12/1966 | Hambling et al. | 585/516 |
| 3,755,491 | 8/1973 | Hashimoto | 585/516 |
| 3,756,963 | 9/1973 | Formi | 585/516 |
| 3,758,416 | 9/1973 | Formi | 585/516 |
| 3,853,786 | 12/1974 | Formi et al. | 585/516 |
| 3,916,019 | 10/1975 | Closson et al. | 585/516 |
| 3,950,450 | 4/1976 | Hashimoto et al. | 585/516 |
| 4,388,480 | 6/1983 | Imai et al. | 585/516 |

*Primary Examiner*—Curtis R. Davis
*Attorney, Agent, or Firm*—McGlew and Tuttle

[57] ABSTRACT

A process for preparing 4-methyl-1-pentene comprising dimerizing propylene in the presence of a catalyst, characterized in that the catalyst is composed from the treatment of precatalyst by at least one oxygen-containing compound selected from oxygen, alcohols, ethers, acetals, orthocarboxylates and esters. The precatalyst is composed of element or compound selected from sodium, potassium, sodium amide and potassium amide supported on a carrier principally represented by the following formula (1):

$$K_2O.xAl_2O_3 \qquad (1)$$

wherein x has a value in the range of $0.5 \leq x \leq 11$. In one embodiment, the precatalyst is hydogenated prior to the use thereof.

The use of above mentioned catalyst so remarkably increases the rate of reaction and the selectivity of 4-methyl-1-pentene and allows the reaction rate and selectivity to be kept high for a long period of time.

14 Claims, No Drawings

PROCESS FOR PREPARING 4-METHYL-1-PENTENE

BACKGROUND OF THE INVENTION

1. Field of the Invention

This invention relates to a novel process for producing 4-methyl-1-pentene by the dimerization of propylene.

4-Methyl-1-pentene polymers are excellent in transparency, heat resistance, mechanical and electrical properties and chemical resistance. It is also a compound capable of exhibiting particularly excellent properties as the comonomer for improving various properties of polyolefins, such as transparency, environmental stress crack resistance and like properties.

2. Description of the Prior Art

It has been known that 4-methyl-1-pentene can be obtained by dimerizing propylene in the presence of an alkali metal such as sodium or potassium [reported for example by A. W. Shaw et al in J. Org. Chem., 30, 3286(1965)].

It has also been known to use for example an alcohol (Japanese Patent Publication No. 8701/1963), phenol (Japanese Patent Publication No. 19622/1964) or tertiary amine (Japanese Patent Laid-open No. 93303/1974) when conducting the dimerization reaction of propylene in the presence of an alkali metal.

It has also been known that 4-methyl-1-pentene can be obtained by dimerizing propylene in the presence of an alkali metal supported on a carrier. In this case, graphite, potassium carbonate, alkali metal silicates, alkali metal halides, magnesium sulfate, talc or the like may be used as the carrier.

However, the above-mentioned and the other known processes are accompanied by such disadvantages that the yield of propylene dimer and the selectivity of 4-methyl-1-pentene are both relatively low and besides the desired 4-methyl-1-pentene, by-products, such as cis- and trans-4-methyl-2-pentene, 2-methyl-1-pentene, 2-methyl-2-pentene, 1-hexene, cis- and trans-2-hexene and cis- and trans-3-hexene are produced in large amounts. The boiling points of these isomers are close to the desired product, 4-methyl-1-pentene, and therefore, a high degree of fractionation is required to obtain 4-methyl-1-pentene in sufficiently high purity. This becomes another disadvantage because of high cost for purification.

Further, catalysts used in the known processes will take a long induction periods, i.e., they require a great deal of time until their full activities are exhibited. In other words, they require a long period of time until the reaction proceeds stationarily. Hence, many of these known processes were inferior from the viewpoint of economy and stable operation. Moreover, many of these known dimerizing catalysts have not only a capability of catalytic dimerization but also a capability of catalytic polymerization. Polymerization reactions is allowed to proceed along with the dimerization reaction, and the polymers so produced deposit on the surfaces of such catalyst, resulting in the gradual loss of their activities. It is often observed that the selectivity tends to decrease as the activity decreases, particularly when such a catalyst is used. A catalyst which has lost its activity in the above manner solidified with resinous polymers in the reactor. However, it internally contains still sufficiently highly active portions. When such a spent catalyst is drawn out for replacement with a fresh catalyst, there is thus a potential danger that it may burn or induce fire due to contact with oxygen, water or the like in the air. Thus, such catalysts are accompanied by the further disadvantage that their handling is inconvenient.

In the conventional catalysts used for the production of 4-methyl-1-pentene, the amounts of sodium or potassium supported on carriers were below 5 wt. %, usually within the range of 1–3 wt. % or so because the carriers have relatively small pore volume. When more than 5 wt. % of sodium or potassium is attempted to be loaded on the carrier, these alkali metals deposited in the form of mud on the surfaces of the carriers. Thus, the catalysts agglomerated into lumps, thereby not only making their industrial handling difficult but also significantly lowering their dimerization activities in many cases. In order to carry out the dimerization reaction with fixed-bed method, it is necessary to form each catalyst into pellets. It was however impossible to pelletize potassium carbonate which has been conventionally used as a carrier for 4-methyl-1-pentene catalysts, because it does not have caking property by itself. Thus, many of known catalysts were prepared by producing pellets using graphite or the like as a binder and then thus-produced pellets were treated by sodium or potassium. These pellets were however accompanied by such a disadvantage that their service life as catalysts became short due to their low mechanical strength which relates to their tendency of disintegration during their use.

SUMMARY OF THE INVENTION

An object of this invention is to improve the drawbacks of conventionally-known processes and catalysts such as those mentioned above and to provide a process for preparing 4-methyl-1-pentene by using a catalyst which has been improved in both propylene-dimerization activity and 4-methyl-1-pentene selectivity.

The present inventors conducted an extensive investigation in an attempt to make improvements of the above-described disadvantages of conventionally-known processes and catalysts, resulting in the finding of a process which makes use of the novel catalyst system disclosed in U.S. Pat. No. 4,388,480. In the thus-found process, propylene was dimerized using a catalyst which composed of sodium and/or sodium amide supported on a carrier having a composition represented by the following formula (1):

$$K_2O \cdot xAl_2O_3 \qquad (1)$$

wherein $0.5 \leq x \leq 11$, preferably $1 \leq x \leq 5$ or using such a catalyst previously treated with hydrogen, to obtain 4-methyl-1-pentene. According to this process, it was possible not only to overcome the drawbacks with which processes making use of various conventional catalysts were accompanied but also to enable the carrier bear more sodium so as to increase the reaction rate and the selectivity of 4-methyl-1-pentene to considerable extents and at the same time, to maintain such activities and selectivity at high levels for a very long period of time.

The present inventors have proceeded with a further investigation on the above-mentioned process. As a result, it has been found that the preparation process of 4-methyl-1-pentene, which process relies upon the dimerization of propylene, can be improved in an absolutely-unexpected manner, leading to accomplishment of this invention.

When used as a catalyst, alkali metals or organoalkali metal compounds are normally kept out of contact with oxygen-containing compounds such as water, oxygen, alcohols and esters because the alkali metals or organoalkali metal compounds undergo reactions with such oxygen-containing compounds and loses its catalytic activities. It has however been surprisingly found by the present inventors that when at least one element or compound selected from the group consisting of sodium, potassium, sodium amide and potassium amide is carried on the compound represented by the above formula (1) as a carrier for the reaction catalyst, which may in some instances still contain in a mixed form an excess amount of unreacted potassium carbonate used as a starting material for the production of the support, and is then either directly or after treated with hydrogen brought into contact with at least one oxygen-containing compound selected from the group consisting of oxygen, alcohols containing 1-5 carbon atoms, ethers represented by the following formula (2):

$$R^1OR^2 \quad (2)$$

wherein $R^1$ and $R^2$ mean individually a hydrocarbon residual group containing 1-5 carbon atoms, acetals represented by the following formula (3):

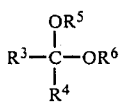

(3)

wherein $R^3$, $R^4$ and $R^5$ denote individually a hydrogen atom or hydrocarbon residual group containing 1-5 carbon atoms and $R^6$ means a hydrocarbon residual group containing 1-5 carbon atoms, orthocarboxylates represented by the following formula (4):

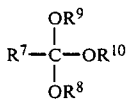

(4)

wherein R is a hydrogen atom or a hydrocarbon residual group containing 1-5 carbon atoms, and $R^8$, $R^9$ and $R^{10}$ mean individually a hydrocarbon residual group containing 1-5 carbon atoms, and esters represented by the following formula (5):

$$R^{11}COOR^{12} \quad (5)$$

wherein $R^{11}$ means a acyclic or cyclic, aliphatic hydrocarbon residual group or an aryl or aralkyl group containing 6-20 carbon atoms, and $R^{12}$ means a hydrocarbon residual group containing 1-5 carbon atoms, the catalyst is by no means deactivated but depending on the amount of the thus-contacted oxygen-containing compound, its dimerization activity and its selectivity of 4-methyl-1-pentene are conversely improved or even if its activity is somewhat reduced, its selectivity of 4-methyl-1-pentene is significantly improved.

In Japanese Patent Publication No. 8701/1963 referred to above upon dimerization of propylene in the presence of the alkali metal as a catalyst, it was attempted to enhance the activity of an alkali metal catalyst by adding a small amount of an alcohol containing 8 or more carbon atoms, an acid or an aldehyde to the alkali metal. The process which the present inventors have found and then accomplished is different in nature from the process disclosed in the above patent publication. Namely, when alcohols containing 1-5 carbon atoms out of alcohols containing 1-7 carbon atoms which described not effective in the above patent publication are used in amounts substantially equal to those described in the Examples of the above patent publication in the present invention, the selevtivity is improved and at the same time, the activity is also improved significantly. However, use of alcohols containing 8 or more carbon atoms, which are said to be effective in the above patent publication, result in a reduction in both activity and selectivity. Further, alcohols containing 1-5 carbon atoms were totally ineffective and lowered the activity of the catalyst system to a significant extent when which were acted on a supported catalyst system, namely, a known catalyst system containing metallic sodium carried on potassium carbonate. After all, the catalyst system of the present invention appears to have provided new sites for the reaction as a result of some sort of action of the compound represented by the formula (1) with an oxygen containing compound including for example an alcohol which contains 1-5 carbon atoms.

DETAILED DESCRIPTION OF THE PREFERRED EMBODIMENTS

The compound represented by the formula (1), which is used as a principal component of a carrier in the process of this invention, may be obtained by the following method: The method comprises (i) at least one potassium-containing compound such as KOH, $KOR^{13}$ wherein $R^{13}$ denotes a $C_1$-$C_{20}$ linear or branched aliphatic hydrocarbon residual group or a $C_6$-$C_{30}$ aryl or aralkyl group, $KHCO_3$, $K_2CO_3$ (hydrous or anhydrous), KH or $KR^{14}$ wherein $R^{14}$ is at least one member selected from $C_1$-$C_{20}$ linear or branched aliphatic hydrocarbon residual groups $C_6$-$C_{30}$ aryl or aralkyl group is mixed with (ii) at least one aluminum-containing compound such as a hydrated alumina, e.g., hydrogilite, bialite, boehmite, diaspore, $\alpha$- and $\gamma$-alumina, and Al-$(OR^{15})_3$ wherein $R^{15}$ is at least one member selected from $C_1$-$C_{20}$ linear or branched aliphatic hydrocarbon residual groups, $C_6$-$C_{20}$ aryl or aralkyl groups in such proportions that the K/Al ratio has the above-defined x value. The thus-obtained mixture is then reacted, usually at 400°-2000° C., preferably at 500°-1500° C., in the presence or absence of air, nitrogen or the like for 1-20 hours. In the compound represented by the formula (1), x is preferable in the range of $1 \leq x \leq 5$.

The carrier so obtained is expressed herein as having $K_2O$ and $Al_2O_3$ as its components, however this expression is used merely for the sake of convenience to indicate the composition of a carrier produced from the various composition of starting reagents. Thus these components do not exist in their own forms but are contained principally as a double oxide form in the carrier. Accordingly, even if $K_2O$ and $Al_2O_3$ are merely mixed, the resulting carrier will be essentially different from those obtained in the present invention and will not allow a catalyst supported thereon to exhibit such high catalytic activity and high selectivity expected from the use of the catalyst of the present invention:

When potassium carbonate is used as a potassium source which is one of raw materials for the carrier of present invention, in case that potassium carbonate is used in such as amount that x becomes smaller than 0.5, namely, $x<0.5$, the same improvements as those available when x has a value in the range of $0.5 \leq x \leq 11$ can be brought about. In other words, when potassium carbonate is employed as potassium source an excess amount of potassium carbonate still left in its unreacted form in the carrier may be handled in exactly the same manner as the compound represented by the formula (1). So the carrier may be either the compound represented by the formula (1) above or a carrier containing the compound represented by the formula (1) as its principal component in combination with a small amount of unreacted potassium carbonate. In this case, the amount of still-remaining potassium carbonate is preferably 30 wt. % of the compound represented by the formula (1) or less.

Since the carrier represented by the formula (1) of this invention, can very rapidly absorb and carry thereon a large amount of sodium, or potassium, or their hydride or a amide, and can be kept in the state of a very good dispersion, the resultant material is a very excellent catalyst precursor even as is or after hydrogen treatment if desired. The precursor can form a catalyst capable of exhibiting still higher activity and selectivity in the dimerization reaction of propylene when it is brought into contact with at least one oxygen-containing compound selected from the group consisting of oxygen, alcohls containing 1-5 carbon atoms, ethers represented by the formula (2), acetals represented by the formula (3), orthocarboxylates represented by the formula (4) and esters represented by the formula (5) (hereinafter called "the oxygen-containing compound" for the sake of brevity) with the methods described hereinafter.

The above mentioned catalyst system, which are excellent in dispersibility, non-coagulation, activity and selectivity and requires no appreciable induction period of time before the start of the reaction, is very suitable for the dimerization reaction in continuous stirred tank system in which the catalyst may be continuously fed with propylene.

Unlike potassium carbonate, the compound represented by the formula (1) which is a principal component of the carrier useful in the practice of this invention may be formed into pellets having very high strength by forming a kneaded mixture of the above-mentioned raw materials by a known method such as the extrusion molding method or the press forming method and then calcining the thus-formed mixture. The thus-pelletized carrier which contains the compound of the formula (1) as its principal component is the most suitable for the production of 4-methyl-1-pentene in fixed-bed method, because the pellets can absorb very rapidly and carry thereon a large amount of sodium, potassium or a hydride or a amide or the like as powder state and the strength of the pellets is not reduced even after being brought into contact with the oxygen-containing compound for its treatment in accordance with the process of this invention, and it can achieve high activity and selectivity in the dimerization reaction of propylene.

The shape of the carrier to be used in the process of this invention may be chosen from various desired shapes ranging from fine powder to beads or rods of about 10 mm in diameter or length, depending on the manner of each reaction, the shape and volume of each reactor, etc. Namely, the carrier useful in the practice of the process of this invention may be produced with desired shape and size by subjecting lumps of the compound represented by the formula (1), which has been obtained by calcining the raw materials for the carrier, to crush and subsequent classification, or by mixing and kneading the raw materials, pelletizing the thus-kneaded mixture by such a method as extrusion molding or press forming and then calcining the thus-pelletized mixture.

Regardless of the shape of the carrier, namely, whether the carrier is powder or pellets, sodium and/or potassium can be carried on the carrier in the same manner.

Methods of carrying sodium and/or potassium on the carrier of this invention include a method of mixing under agitation sodium and/or potassium and the carrier in the absence of solvent at 120°-400° C., a method of depositing sodium and/or potassium vapor on the carrier.

Methods for carrying sodium amide or potassium amide on the carrier comprises immersing the carrier in an ammonia solution of sodium amide or potassium amide, the solution being prepared by dissolving sodium or potassium in liquid ammonia, to fully impregnate the carrier with the solution and evaporating the ammonia from the solution-impregnated carrier to obtain a catalyst.

The amount of sodium, potassium, sodium amide or potassium amide (hereinafter called "an alkali metal" for the sake of brevity) to be carried on the carrier may preferably range from 0.1 to 20 wt. % as sodium and/or potassium atom. Even when the carried amount of alkali metals is of very high level, namely, as much as 20 wt. %, by-products such as tar and resinous materials are hardly produced. And the catalysts exhibit high resistance against water, moisture and other impurities brought into the reaction system owing to the large amount of alkali metals are carried. Thus, the present catalysts may maintain high activity and selectivity for a long period of time. Needless to say, it is clear that even the catalysts having alkali metals carried in amounts of as small as 0.1-1 wt. % may be used without any trouble in the practice of the process of this invention although the activity will be somewhat reduced. In practice, catalyst carrying 1-15 wt. % of the alkali metal are preferably used.

The thus-obtained catalysts may embrace the catalysts used in the process of the above-referred to U.S. Pat. No. 4,388,480, which have by themselves catalytic activities for the dimerization reaction of propylene. However, these catalysts are handled as catalyst precursors in the process of this invention. Prior to the treatment of such catalyst precursors with the oxygen-containing compounds which will be described further herein, the catalyst precursors may optionally be treated with hydrogen, for example, at temperatures in the range of 150°-400° C., at pressures up to 100 kg/cm$^2$ and for 0.5-10 hours.

The thus-obtained catalyst precursors are then brought into contact with at least one oxygen-containing compound as described above.

Alcohols containing 1-5 carbon atoms which may be either saturated or unsaturated, includes methanol, ethanol, n-propanol, isopropanol, n-butyl alcohol, sec-butyl alcohol, isobutyl alcohol, t-butyl alcohol, pentanol, allyl alcohol, methallyl alcohol and so on. Among these alcohols, methanol, ethanol and isopropanol are preferred with ethanol being particularly preferred.

Specific examples of the ethers represented by the formula (2) may include methyl ether, methyl ethyl ether, ethyl ether, allyl ethyl ether, ethyl pentyl ether, isopropyl ether, etc.

As illustrative specific acetals represented by the formula (3), may be mentioned acetals such as formaldehyde dimethyl acetal, formaldehyde diethyl acetal, formaldehyde dipentyl acetal, acetaldehyde dimethyl acetal, acetaldehyde diethyl acetal, acetaldehyde diisobutyl acetal, propionaldehyde diethyl acetal, propionaldehyde methyl isobutyl acetal, n-butylaldehyde dimethyl acetal, isobutylaldehyde diethyl acetal and valeroaldehyde diethyl acetal, as well as ketals such as acetone dimethyl acetal, acetone diethyl acetal, acetone diisopropyl acetal, acetone dipentyl acetal, ethyl ketone dimethyl acetal, ethyl ketone diethyl acetal and ethyl ketone diisobutyl acetal.

Exemplary specific orthocarboxylates represented by the formula (4) may embrace trimethyl orthoformate, triethyl orthoformate, isoamyl orthoformate, methyl diethyl orthoacetate, triethyl orthoacetate, triethyl orthobutyrate, trimethyl orthovalerate, and so on.

As specific examples of the esters represented by the formula (5), may be mentioned methyl formate, ethyl formate, ethyl acetate, isopropyl acetate, pentyl acetate, methyl propionate, ethyl propionate, butyl butyrate, ethyl acrylate, ethyl methacrylate, methyl benzoate, ethyl benzoate, etc.

The methods of treating the catalyst precursor with the above-mentioned oxygen-containing compound are as follows: the oxygen-containing compound may be diluted with a liquid inert to the alkali metal, such as an aliphatic hydrocarbon or a gas such as an inert gas prior to its contact with the catalyst precursor irrespective whether the catalyst precursor is in a powder form or in a pellet form. Here, it is necessary to pay attention to avoid any localized excess reaction between the oxygen-containing compound and the alkali metal on the catalyst precursor and hence to ensure uniform treatment of the oxygen-containing compound by incorporating such measures as reduction of the concentration of the oxygen-containing compound to a sufficiently low level and/or application of sufficient agitation, because the alkali metal carried on the carrier has high reactivity. As diluents useful in the above measure, it is preferred to employ saturated aliphatic hydrocarbons containing 6 or more carbon atoms, such as hexane, heptane, octane, dodecane or the like, or an inert gas such as nitrogen, helium or argon. When treating the catalyst precursor with oxygen in a hydrocarbon, it is necessary to pay special attention to maintain the concentration of oxygen below its flammability limit because the alkali metal is reacted with oxygen in the presence of the combustible material.

The concentration of oxygen as oxygen-containing compound and its treatment temperature may be 0.001–5.0 vol. % and $-20°-400°$ C., or suitably $0°-100°$ C., respectively. In the case of an alcohol containing 1-5 carbon atoms, the ranges of 0.001 -5.0 vol. % and $-20°-200°$ C. or preferably $0°-100°$ C. are suited. Where an ether of the formula (2), an acetal of the formula (3) or an orthocarboxylate of the formula (4) is used as the oxygen-containing compound, the ranges of 0.01-50 vol. % and $0°-300°$ C. or preferably $20°-200°$ C. are preferred.

The amount of the oxygen-containing compound to be brought into contact with the catalyst precursor in order to prepare a catalyst system in the process of this invention may be 0.1–20 mole % or preferably 0.3–10 mole % for oxygen, and 0.5–80 mole % or preferably 1–50 mole % for the above-mentioned oxygen-containing compounds other than oxygen, both based on the alkali metal carried on the carrier containing the compound of the formula (1) as its principal component. If the amount of the oxygen-containing compound is lower than the lower limit of its corresponding range, it will not be able to bring about its effect, which is necessary for the process of this invention, to any satisfactory extent. On the other hand, the amount of the oxygen-containing compound exceeds the upper limit of its corresponding range, the activity of the resulting catalyst system will be lowered, its service life will be shortened and it will hence be rendered uneconomical, although its selectivity will still be kept at a high level in the dimerization reaction.

When using oxygen as the oxygen-containing compound, some modified methods may exist besides the above-described simple treatment through the mutual contact of the catalyst precursor and oxygen. In the first modification, the, so called catalyst precursor is reacted with propylene and is thereafter treated with oxygen. The second modification comprises bringing the catalyst precursor into contact with oxygen, contacting and reacting the oxygen-reacted catalyst precursor with propylene and then contacting and treating the resultant catalyst precursor again with oxygen. According to the third modification, upon practicing the dimerization reaction of propylene in the presence of the catalyst precursor, propylene which contains 2–500 ppm by weight or more preferably 10–200 ppm by weight of oxygen is used whereby the catalyst precursor becomes catalyst. Propylene containing substantially no oxygen mixed therein has heretofore been used as the raw material, or if some oxygen existed therein, it has been used after removal of the oxygen.

The above-described concentration of oxygen can be attained by dissolving under pressure oxygen in propylene. If the concentration of oxygen in propylene should be lower than 2 ppm by weight, it will take a considerably long period of time until the effect of treatment of the catalyst precursor with oxygen in accordance with this invention is exhibited. Therefore, use of such a low oxygen concentration is impractical. On the other hand, any oxygen concentrations higher than 500 ppm by weight in propylene will cause the propylene and oxygen to react with each other, leading to the formation of resinous matter. This resinous material will causes coking in the reactor. Therefore, such high oxygen concentrations are not suitable.

Whichever modifications are employed for the treatment of the catalyst precursor with oxygen, it is preferred to control the treatment in such a way that the cumulative amount of oxygen falls within the range of 0.1–20 mole % or preferably 0.3–10 mole %, both based on the alkali metal.

Especially in the above-described third modification, it may not be considered to be fully suitable to use propylene having the above-mentioned oxygen concentration continuously from the initiation of use of the catalyst precursor to the loss of its catalytic life. Since oxygen contained in the raw material, namely, propylene undergoes a substantially stoichiometric reaction with the alkali metal carried on the catalyst support, it is preferred to proceed with the dimerization reaction by switching the oxygen-containing propylene to another supply of propylene, which has an extremely low oxygen content or is absolutely free of oxygen, when the cumulative amount of oxygen subjected to contact with the catalyst precursor for its treatment has reached the above-described range.

According to the process of this invention which makes use of a catalyst treated with the oxygen-containing compound in the above-described manner, the dimerization activity for propylene and the selectivity of 4-methylene-1-pentene are significantly improved depending on the amount of the oxygen-containing compound used for the treatment of the catalyst precursor. Although reasons for the above effects have not yet fully elucidated to date, it may probably be assumed that the electronic circumstances are changed around active sits consisted of the alkali metal on the carrier due to the treatment of the catalyst precursor with the oxygen-containing compound and the coordination of propylene is limited so as to promote dimerization and at the same time to suppress isomerization.

Another important feature of the process of this invention is that when a fresh supply of the catalyst according to this invention has been introduced into the reactor will have very short induction period. On the contrary the conventional catalyst systems known to date, have been found to require such induction periods of 10-15 hours at the shortest and more than several days at the longest.

Upon practice of the dimerization reaction of propylene in accordance with the process of this invention, a variety of reaction methods may be contemplated. It may for example be possible to adopt batch or semi-batch method using an autoclave, continuous stirred tank method using an autoclave into which the catalyst and propylene are fed, continuously, and fixed-bed continuous reaction method in which the catalyst is packed in a reactor and then propylene is supplied.

Whichever reaction method of the above-mentioned reaction methods is used, it is feasible to carry out the reaction by using as a solvent aliphatic hydrocarbons such as heptane, octane or dodecane, or a mixture thereof, or a compound which does not induce any side reaction in the process of this invention.

The dimerization of propylene according to the process of this invention may be effected at a temperature of 100°-250° C., preferably 140°-180° C., and at a pressure of 20-200 kg/cm$^2$.

When using an autoclave, there is no special limitation imposed on the amount of the catalyst relative to propylene, however in practice, it may be preferable to limit the amount of the catalyst within the range of 0.5-20 wt. %. The term "the amount of the catalyst" used herein is intended to mean the total weight of the carrier and the alkali metal supported on the carrier.

The reaction time (in the case of the batch or semi-batch method) or the residence time (in the case of the continuous methods) may preferably within the range of 1-10 hours. In the fixed-bed continuous method, the preferred liquid hourly space velocity (LHSV) may range from 0.1 to 10 (V/V.hr).

Propylene which may be used in this invention may not necessarily be of high purity, however, it is preferred to employ propylene from which other olefines, diolefines, water, air, carbon dioxide and the like have been removed to such extents as generally available in the industry. Further, it is preferred that saturated hydrocarbons such as ethane, propane, butane and the like are not contained in propylene. However, propylene containing such hydrocarbons may still be used without troubles.

The invention will hereinafter be described specifically by the following Examples.

EXAMPLE 1

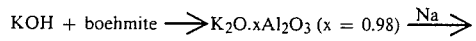

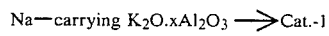

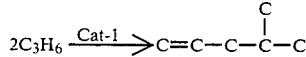

Comminuted into fine powder were 66 g of potassium hydroxide pellets (water content: 15%), followed by its thorough mixing with 80 g of boehmite. The thus-prepared mixture was placed in an alumina-made crucible for calcination at 1200° C., for 5 hours, in an air atmosphere. After allowing the thus-calcinated mixture to cool down, it was taken out of the crucible and then placed in an aluminum-made pot. It was ground for 2 hours in a centrifugal ball mill. Particles finer than 60 mesh were used as a carrier. The K/Al ratio of the carrier was determined by the atomic absorption analysis to be K/Al=0.98.

Sixty grams of the carrier were heated to 150° in a nitrogen gas atmosphere in a three-necked flask having an internal volume of 300 ml, to which 6 g of sodium was added with stirring. After the addition, the temperature was raised to 200° C., at which the stirring was continued for further one hour. A catalyst precursor in which the sodium was carried uniformly was obtained.

Sixteen grams of the thus-obtained catalyst precursor was charged in a autoclave which had in advance been dried sufficiently and purged with nitrogen. The autoclave was made of stainless steel and had a volume of 1000 ml. One hundred milliliter of n-nonane were poured as a dispersant to the autoclave. The valve of the autoclave was connected to a U-shaped mercury manometer, and air, which had been dried through "Molecular Sieve 3A", was charged to 150 mmHg when measured by a mercury manometer. While driving the stirrer, the catalyst precursor was subjected to an oxygen treatment until the indicator of the manometer dropped to 130 mmHg. At this stage, air was released from the autoclave and the autoclave was purged with nitrogen gas. In the above procedure, oxygen in an amount equivalent to 1.5 moles of the carried sodium was used for the treatment of the catalyst precursor.

The dimerization reaction of propylene was conducted using the thus-obtained catalyst in the following manner. Namely, 150 g of propylene was charged in the autoclave and the reaction was carried out at 160° C. for 5 hours. After completion of the reaction, the autoclave was rapidly cooled with water to terminate the reaction. Unreacted propylene was collected in a trap which was placed in a dry ice/methanol bath. Furthermore, the solvent, reaction products, etc. which remained in the autoclave were recovered by distillation under reduced pressure. Propylene which had beforehand been collected in the trap was caused to evaporate, thereby providing a residue having a boiling point not lower than that of the propylene dimer. The residue was then incorporated with the above-recovered liquid reaction mixture. The resulting mixture was analyzed by gas chromatography, using a squalane-coated capillary glass column of 50 m long. The conversion of propylene was 49% while the selectivity of 4-methyl-1-pentene was 92%. Therefore, the activity of the above catalyst per gram and hour was 0.919 (g-dimer/g-catalyst.hr) [this unit will be omitted in the subsequent Examples.].

Comparative Example 1

The dimerization reaction of propylene was conducted under exactly the same conditions as in Example 1 except that the catalyst precursor was not contacted with oxygen for its treatment. As a result of an analysis, the conversion of propylene and the selectivity of 4-methyl-1-pentene were 34% and 89%, while the activity of the catalyst was 0.638.

EXAMPLE 2

Charged in an autoclave which had in advance been thoroughly dried and purged with nitrogen was 16 g of a catalyst precursor prepared as in Example 1. The autoclave was made of stainless steel and had a volume of 1000 ml. After adding 100 ml of n-heptane containing 0.43 wt. % of ethanol to the catalyst precursor, the resultant mixture was stirred at room temperature for 30 minutes. Subsequent to cooling the autoclave, a portion of the liquid reaction mixture was sampled out for its analysis by gas chromatography. It was found that the charged ethanol was used up substantially in its entirety. Thus, ethanol in an amount equivalent to 10 mole % of the carried sodium was brought into contact with the catalyst precursor for its treatment in the above procedure.

Using the thus-obtained catalyst, the dimerization reaction of propylene was carried out under exactly the same conditions as those employed in Example 1. As a result of an analysis, the conversion of propylene and the selectivity of 4-methyl-1-pentene were respectively 42% and 93%, accordingly the activity of the catalyst was 0.788.

EXAMPLES 3–20

Various catalysts were prepared by treating the catalyst precursor as in Example 2 except that instead of the treatment of the catalyst precursor with 100 ml of ethanol-containing n-heptane in Example 2, the amount of n-heptane, the kind and amount of the oxygen-containing compound contained in n-heptane, and the treatment conditions were varied as shown in Table 1. Using these catalysts, the dimerization reaction of propylene was carried out under exactly the same conditions as those employed in Example 1 except that the reaction time was changed. Results are also given in Table 1.

Comparative Examples 2–6

Various catalysts were prepared by treating the catalyst precursor as in Example 2 except that instead of the treatment of the catalyst precursor with 100 ml of ethanol-containing n-heptane in Example 2, the kind and amount of the oxygen-containing compound contained in the n-heptane and the treatment conditions were varied as shown in Table 1. Using these catalysts, the dimerization reaction of propylene was carried out under ecactly the same conditions as those employed in Example 1. Results are also shown in Table 1.

TABLE 1

| | Treatment of catalyst precursor with oxygen-containing compound | | | | | | Results of dimerization reaction | | |
|---|---|---|---|---|---|---|---|---|---|
| Example | Oxygen-containing compound | Amount of n-heptane used (ml) | Treatment temperature (°C.) | Treatment time | Diluted concentration (wt. %) | Treated amount (mole %) | Reaction time (hrs.) | Conversion of propylene (%) | Selectivity of 4-methyl-1-pentene (%) | Activity of catalyst |
| 3 | Ethanol | 100 | Room temp. | 30 min. | 0.09 | 2 | 5 | 42 | 93 | 0.788 |
| 4 | Ethanol | 100 | Room temp. | 30 min. | 2.14 | 50 | 5 | 29 | 92 | 0.544 |
| 5 | Methanol | 300 | Room temp. | 30 min. | 0.2 | 20 | 3 | 41 | 90 | 1.280 |
| 6 | Isopropyl alcohol | 100 | Room temp. | 30 min. | 0.28 | 5 | 5 | 38 | 92 | 0.713 |
| 7 | Isoamyl alcohol | 100 | Room temp. | 30 min. | 0.82 | 10 | 5 | 33 | 90 | 0.619 |
| 8 | Ethyl acetate | 100 | 100 | 1 hr. | 0.83 | 10 | 5 | 37 | 93 | 0.694 |
| 9 | Ethyl acetate | 100 | 100 | 1 hr. | 0.17 | 2 | 5 | 35 | 93 | 0.656 |
| 10 | Ethyl acetate | 100 | 100 | 1 hr. | 4.13 | 50 | 5 | 32 | 92 | 0.600 |
| 11 | Methyl acetate | 300 | 100 | 1 hr. | 0.46 | 20 | 3 | 42 | 91 | 1.313 |
| 12 | Ethyl benzoate | 100 | 100 | 1 hr. | 1.41 | 10 | 5 | 31 | 90 | 0.581 |
| 13 | Ethyl ether | 100 | 160 | 6 hrs. | 1.4 | 20 | 5 | 41 | 93 | 0.769 |
| 14 | Ethyl ether | 100 | 160 | 6 hrs. | 0.14 | 2 | 5 | 37 | 93 | 0.694 |
| 15 | Ethyl ether | 100 | 160 | 6 hrs. | 3.48 | 50 | 5 | 34 | 93 | 0.638 |
| 16 | Formaldehyde diethyl acetal | 100 | 160 | 4 hrs. | 2.04 | 20 | 5 | 39 | 92 | 0.709 |
| 17 | Triethyl orthoacetate | 100 | 160 | 4 hrs. | 3.05 | 20 | 5 | 36 | 93 | 0.675 |
| 18 | Methyl ether | 100 | 160 | 6 hrs. | 0.30 | 10 | 5 | 42 | 92 | 0.788 |
| 19 | Acetone dimethyl acetal | 100 | 160 | 4 hrs. | 2.04 | 20 | 5 | 41 | 92 | 0.769 |
| 20 | Triethyl orthovalerate | 100 | 160 | 4 hrs. | 3.84 | 20 | 5 | 35 | 93 | 0.656 |
| Comp. Ex. 2 | n-Octanol | 100 | Room temp. | 30 min. | 1.21 | 10 | 5 | 18 | 37 | 0.338 |
| Comp. Ex. 3 | n-Octanol acetate | 100 | 100 | 1 hr. | 1.62 | 10 | 5 | 20 | 44 | 0.375 |
| Comp. Ex. 4 | n-Hexyl ether | 100 | 160 | 6 hrs. | 3.52 | 20 | 5 | 23 | 48 | 0.431 |
| Comp. Ex. 5 | Formaldehyde dihexyl acetal | 100 | 160 | 4 hrs. | 3.92 | 20 | 5 | 22 | 45 | 0.413 |
| Comp. Ex. 6 | Trihexyl orthoacetate | 100 | 160 | 4 hrs. | 6.21 | 20 | 5 | 19 | 41 | 0.356 |

EXAMPLE 21

A catalyst precursor was prepared by supporting 5 wt. % of potassium instead of sodium on the carrier in accordance with procedures similar to those followed in Example 1. Sixteen grams of the thus-obtained catalyst precursor were treated in contact with oxygen in the same manner as in Example 1. The amount of oxygen which was introduced by the oxygen-contacting treatment was equivalent to 5 mole % of the carried potassium. Then, the dimerization of propylene was carried out in the same manner as in Example 1. As a result of an analysis, the conversion of propylene was found to be 36%, the selectivity of 4-methyl-1-pentene was 91% and the activity of the catalyst was 0.614.

EXAMPLES 22-26

Sixteengram portions of a catalyst precursor prepared as in Example 21 were treated with 100 ml n-heptane solutions of their respective oxygen-containing compounds given in Table 2, in the same manner as in Examples 2, 8, 13, 16 and 17, respectively. Using the resulting catalysts, the dimerization reaction of propylene was carried out under the same conditions as those employed in Example 1. Results are also given in Table 2.

EXAMPLE 28

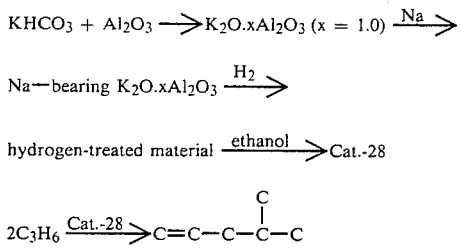

Two hundred grams of potassium hydrogen-carbonate and 202 g of γ-alumina were mixed thoroughly, and the resulting mixture was calcinated at 1000° C. for 7 hours to prepare a carrier. Fifteen grams of the carrier were added with 1.5 g of sodium. The resultant mixture was vigorously stirred at 200° C. for 1 hour to cause the carrier bear the sodium. The thus-obtained sodium-bearing carrier was placed in its entirety in an autoclave made of stainless steel and having an internal volume of 1 liter, followed by an addition of 100 ml of n-heptane as a solvent. After raising the temperature of the contents to 160° C., the autoclave was pressurized to 70

TABLE 2

| Example | Treatment of catalyst precursor with Oxygen-containing compound | | | Results of dimerization reaction | | |
|---|---|---|---|---|---|---|
| | Oxygen-containing compound | Diluted concentration (wt. %) | Treated amount (mole %) | Conversion of propylene (%) | Selectivity of 4-methyl-1-pentene (%) | Activity of catalyst |
| 22 | Ethanol | 0.21 | 5 | 35 | 92 | 0.656 |
| 23 | Ethyl acetate | 0.42 | 5 | 36 | 93 | 0.675 |
| 24 | Ethyl ether | 0.35 | 5 | 34 | 92 | 0.638 |
| 25 | Formaldehyde diethyl acetal | 0.51 | 5 | 33 | 92 | 0.619 |
| 26 | Triethyl orthoacetate | 0.76 | 5 | 33 | 92 | 0.619 |

EXAMPLE 27

A carrier prepared in the same manner as in Example 1 was caused to carry 2% of sodium. Fifty-one grams of the thus-obtained sodium-bearing carrier were then collected in a nitrogen atmosphere in a 300-ml, glass-made, three-neck flask fitted with a stirrer having a blade, which was able to stir and mix powder thoroughly in a solvent-free state, and three way stop-cocks at a each gas introduction port and gas discharge port. Through the flask, a mixed gas consisting of 2% of oxygen and 98% of nitrogen was caused to pass at room temperature, at a velocity of 100 ml/min. and for 15 minutes while stirring the contents. Since the oxygen concentration in the gas discharged from the flask was found to be 0.55% as a result of a measurement, 2 mole % of the whole sodium was treated with the introduced oxygen.

Fifteen grams of the resulting catalyst, 100 ml of n-heptane and 150 g of propylene were placed in an autoclave. The contents were allowed to undergo a reaction at 160° C. for 7 hours. As a result, the conversion of propylene was 29%, the selectivity of 4-methyl-1-pentene was 88% and the activity of the catalyst was 0.414.

kg/cm²G with hydrogen and the contents were then stirred for 3 hours. During this period, a pressure drop of 2.3 kg/cm² was observed. Thus, a hydrogen-treated catalyst precursor was prepared. After allowing the autoclave to cool down and releasing remaining hydrogen, 50 ml of n-heptane containing 0.88 wt. % of ethanol was added and the resultant mixture was stirred at room temperature for 30 minutes. As a result of this procedure, ethanol in an amount equivalent to 10 mole % of the carried sodium was used for the treatment.

One hundred fifty grams of propylene were then charged into the autoclave. The temperature was raised again to 160° C. and the reaction was allowed to proceed for 5 hours. As a result of analysis, it was found that the conversion of propylene was 37%, while the selectivity of 4-methyl-1-pentene and the activity of the catalyst were 92% and 0.673, respectively.

EXAMPLES 29-32

Treated with 50-ml portions of n-heptane containing oxygen-containing compounds shown in Table 3 in the same manner as in Examples 8, 13, 16 and 17, respectively were 16.5 g portions of a hydrogen-treated catalyst precursor prepared in the same manner as in Example 28. Using these catalysts, the dimerization reaction of propylene was conducted under the same conditions as those employed in Example 1. Results are also given in Table 3.

TABLE 3

| Example | Treatment of catalyst precursor with Oxygen-containing compound | | | Results of dimerization reaction | | |
|---|---|---|---|---|---|---|
| | Oxygen-containing compound | Diluted concentration (wt. %) | Treated amount (mole %) | Conversion of propylene (%) | Selectivity of 4-methyl-1-pentene (%) | Activity of catalyst |
| 29 | Ethyl acetate | 1.69 | 10 | 37 | 93 | 0.673 |
| 30 | Ethyl ether | 1.44 | 10 | 38 | 92 | 0.671 |
| 31 | Formaldehyde diethyl acetal | 2.10 | 10 | 37 | 92 | 0.673 |
| 32 | Triethyl orthoacetate | 3.16 | 10 | 36 | 92 | 0.655 |

EXAMPLE 33

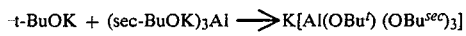

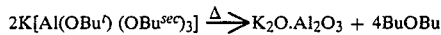

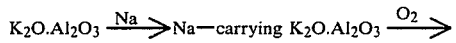

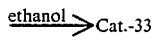

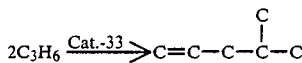

Upon mixing 112 g of t-butoxy potassium and 246 g of aluminum-sec-butoxide at 70° C. in 200 ml of t-butanol in a nitrogen atmosphere, $K[Al(OBu^t)(OBu^{sec})_3]$, an art complex, deposited as a white precipitate. After distillation-off of the solvent, t-butanol under reduced pressure, the resultant precipitate was preliminarily calcinated at 500° C. for 4 hours in a nitrogen stream so as to decompose all organic residues. Thereafter, the temperature was raised to 1200° C. at which the precipitate was calcinated for an additional three hours.

In a nitrogen stream, 6 g of sodium was added to 60 g of the above-obtained carrier. The resultant mixture was agitated at 200° C. for 2 hours, thereby causing the carrier to bear the sodium.

Sixteen grams of the thus-obtained catalyst precursor were placed in an autoclave which had been completely dried beforehand. The autoclave was made of stainless steel and had an internal volume of 1000 ml. To the autoclave, 100 ml of n-heptane was added as a dispersant. The valve of the autoclave was then connected to a U-shaped mercury manometer, and air dried with "Molecular Sieve 3A" was charged to 150 mmHg. While driving the stirrer, the oxygen treatment was allowed to proceed until the reading of the manometor had dropped to 130 mmHg. At this stage, air was released from the autoclave and the autoclave was purged with nitrogen gas. In these procedures, oxygen in an amount equivalent to 1.5 mole % of the carried sodium was used for the containing treatment. Them, 50 ml of n-heptane containing 0.45 wt. % of ethanol was added to the autoclave. The contents were stirred at room temperature for 30 minutes. During this operation, ethanol in an amount equivalent to 5 mole % of the carried sodium was used for the contacting treatment.

One hundred fifty grams of propylene were then added to the autoclave and its reaction was allowed to proceed for 5 hours. As a result of an analysis, it was found that the conversion of propylene was 39%, the selectivity of 4-methyl-1-pentene was 93% and the activity of the catalyst was 0.731.

EXAMPLES 34-37

Treated with 50-ml portions of n-heptane containing oxygen-containing compounds shown in Table 4 in the same manner as in Examples 8, 13, 16 and 17, respectively were 16 g portions of a hydrogen-treated catalyst precursor prepared in the same manner as in Example 33. Using these catalysts, the dimerization reaction of propylene was conducted under the same conditions as those employed in Example 1. Results are also given in Table 4.

TABLE 4

| Example | Treatment of catalyst precursor with Oxygen-containing compound | | | Results of dimerization reaction | | |
|---|---|---|---|---|---|---|
| | Oxygen-containing compound | Diluted concentration (wt. %) | Treated amount (mole %) | Conversion of propylene (%) | Selectivity of 4-methyl-1-pentene (%) | Activity of catalyst |
| 34 | Ethyl acetate | 0.83 | 5 | 40 | 93 | 0.750 |
| 35 | Ethyl ether | 0.70 | 5 | 40 | 92 | 0.750 |
| 36 | Formaldehyde diethyl acetal | 1.02 | 5 | 39 | 92 | 0.731 |
| 37 | Triethyl orthoacetate | 1.53 | 5 | 37 | 92 | 0.674 |

EXAMPLE 38

Three grams of sodium were added in a nitrogen stream to 15 g of a carrier prepared following the same procedures as in Example 33. The resultant mixture was vigorously agitated at 200° for 2 hours so as to have the carrier bear the sodium.

The thus-obtained sodium-bearing carrier was charged in its entirety into a 1-liter autoclave made of stainless steel, followed by a further addition of 100 ml of n-heptane. Then, the contents were subjected to an oxygen treatment in the same manner as in Example 1. The amount of oxygen used for the treatment was 2 mole % of the sodium. Then, 50 g of propylene was added. The contents were then reacted at 160° C. for 2 hours to effect organometallization. Thereafter, unreacted propylene, the resultant dimer and the solvent, n-heptane, were caused to evaporate off. The residue was again subjected to an oxygen treatment in dry air. The amount of oxygen used for the treatment was 2 mole % of the sodium.

The dimerization of propylene was carried out using the thus-obtained catalyst. Namely, 100 ml of n-heptane and 150 g of propylene were added to the autoclave. They were reacted at 150° C. for 4 hours. As a result of an analysis, it was found that the conversion, the selectivity of 4-methyl-1-pentene and the activity were 37%, 89% and 0.686, respectively.

EXAMPLE 39

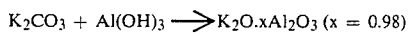

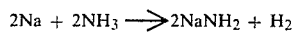

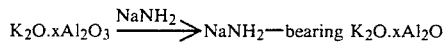

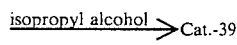

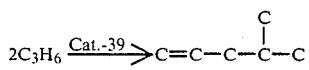

One hundred grams of anhydrous potassium carbonate and 78.0 g of aluminum hydroxide were each ground to obtain particles having a particle size of smaller than 16 mesh. After mixing these two compounds thoroughly together, the mixture was calcinated at 1100° C. for 5 hours to prepare a carrier. The K/Al ratio of the carrier was measured by atomic absorption analysis, resulting in K/Al=1.45. On the other hand, according to the calculation of the amount of carbon dioxide generated by the neutralization with acid of the thus-formed carrier, it was found that 32 g of unreacted potassium carbonate was still left and x was 0.98 in $K_2O \cdot xAl_2O_3$.

Charged in an autoclave made of stainless steel were 15.0 g of the above-prepared carrier and 1.0 g of sodium, followed by an addition of 30 of liquefied ammonia. After stirring the contents at room temperature for 2 hours, ammonia and hydrogen which occurred by the reaction were released to prepare a catalyst precursor. Thereafter, 100 ml of n-heptane containing 0.20 wt. % of isopropyl alcohol was added to the autoclave. The contents were stirred for 30 minutes. By these procedures, isopropyl alcohol in an amount equivalent to 5 mole % of the carried sodium amide was subjected to the contacting treatment.

The dimerization of reaction of propylene was carried out using the above-obtained catalyst. Namely, 150 g of propylene was placed in the autoclave and was then reacted at 150° C. for 5 hours. Then, the reaction mixture was subjected to post treatments in the same manner as in Example 1. An analysis of the reaction product gave the propylene conversion of 19%, the 4-methyl-1-pentene selectivity of 92% and the activity of 0.356.

EXAMPLE 40

The dimerization reaction of propylene was conducted in exactly the same manner as in Example 39, except that a catalyst was used, which obtained by adding 100 ml of n-heptane containing 0.28 wt. % of isopropyl formate in place of the n-heptane containing isopropyl alcohol and stirring the resultant mixture at 100° C. for 1 hour so as to subject isopropyl formate in an amount equivalent to 5 mole % of the carried sodium amide to the contacting treatment. As a result of an analysis, it was found that the conversion of propylene, the selectivity and the activity of the catalyst were 21%, 93% and 0.394, respectively.

EXAMPLE 41

Using potassium instead of sodium, the carrier obtained in Example 39 was caused to carry potassium amide. Conditions for the amidation and the like were exactly the same as those employed in Example 39. Ethanol in an amount equivalent to 20 mole % of the carried potassium amide was consumed for the contacting treatment.

Using the above-prepared catalyst, the reaction was carried out at 160° C. for 5 hours. As a result of an analysis, it was found that the conversion of propylene, the selectivity of 4-methylpentene and the activity of the catalyst were 32%, 92% and 0.600 respectively.

Comparative Example 7

To 100 g of potassium carbonate which had been dried at 500° C. for 5 hours, 2 g of sodium was added in a nitrogen atmosphere. The mixture was agitated vigorously to have the carrier bear the sodium.

Thirty-six grams of the above-prepared catalyst were placed in an autoclave in a nitrogen atmosphere. The autoclave had an internal volume of 1 liter and was made of stainless steel. Then, 150 g of propylene was added together with 100 ml of n-heptane as a solvent. The reaction was carried out at 160° C. for 20 hours. As a result of an analysis, it was found that the conversion of propylene, the selectivity of 4-methyl-1-pentene and the activity of the catalyst were 43%, 75% and 0.090, respectively.

Comparative Example 8

The potassium carbonate carrying 2 wt. % of sodium obtained in Comparative Example 7 was used as a catalyst precursor. Twenty-eight grams of the thus-obtained catalyst precursor were placed in an autoclave which had in advance been thoroughly dried and purged with nitrogen. The autoclave was made of stainless steel and had an internal volume of 1 liter. To the autoclave, 100 ml of n-heptane containing 0.03 wt. % of ethanol was added. The contents were stirred at room temperature for 30 minutes. Owing to this operation, ethanol in an amount equivalent to 2 mole % of the carried sodium was used for the contacting treatment. The dimerization reaction of propylene was carried out using the thus-obtained catalyst. Namely, 150 g of propylene was charged in the autoclave and was then reacted at 160° C. for 30 hours. As a result of analysis, it was found that the conversion of propylene, the selectivity of 4-methyl-1-pentene and the activity of the catalyst were 35%, 77% and 0.062, respectively.

As apparent from a comparison with Comparative Example 7, it was found that when the carrier was changed to potassium carbonate, the effect of the alcohol-contacting treatment was not observed at all but instead, the activity of the catalyst was lowered.

EXAMPLE 42

In an autoclave with a catalyst precursor carrying sodium amide thereon prepared as in Example 39, 100 ml of n-heptane and 150.0 g of propylene, the reaction was carried out at 160° C. for 8 hours. The contents of the autoclave were subjected to post treatments as in Example 1. Upon its analysis, it was found that the conversion of propylene, the selectivity of 4-methyl-1-pentene and the activity of the catalyst were 37%, 87% and 0.377 respectively.

Then, 100 ml (at normal pressure) of n-heptane was sucked into the autoclave the internal pressure of which was of a negative level due to the post treatments. Dry air was also sucked until the internal pressure reached normal pressure. Owing to this operation, oxygen was introduced in an amount equivalent to 11.0 mole % based on sodium amide carried on the catalyst precursor.

Thereafter, 150 g of propylene was charged into the same autoclave. The propylene was again reacted at 160° C. for 5 hours. As a result of an analysis of the reaction mixture, it was found that the conversion of propylene, the selectivity of 4-methyl-1-pentene and the activity of the catalysts were 32%, 90% and 0.540, respectively.

Comparative Example 9

The dimerization reaction of propylene was again carried out under exactly the same conditions as those employed in Example 42, except that the catalyst, which was reacted with propylene for 8 hours as in Example 42, was not subjected to the oxygen-contacting treatment. As a result, it was found that the conversion of propylene, the selectivity of 4-methyl-1-pentene and the activity of the catalyst were 28%, 86% and 0.452 respectively.

EXAMPLE 43

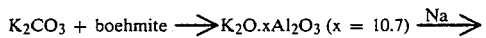

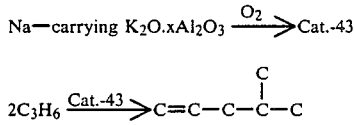

Seventy grams of potassium carbonate and 660 g of boehmite were calcinated at 1800° C. for 7 hours, thereby to obtain a carrier having an Al/K ratio of 10.7. The potassium content is slightly lower than its content in the charge composition. Some potassium seems to have sublimated in the course of the calcination. From an X-ray diffraction diagram of this carrier, the presence of alumina was not observed.

Using the thus-prepared carrier, 5 wt. % of sodium was carried in the same manner as in Example 1. Fifty-five grams of the resulting sodium-bearing carrier were collected and subjected to an oxygen treatment as in Example 33, to obtain a catalyst containing oxygen introduced in an amount of 13 mole % of the sodium. Eighteen grams of the catalyst, 100 ml of n-heptane and 150 g of propylene were charged in an autoclave, in which they were reacted at 150° C. for 6 hours. As a result of an analysis, it was found that the conversion of propylene, the selectivity of 4-methyl-1-pentene and the activity of the catalyst were 24%, 90% and 0.333, respectively.

EXAMPLE 44

The carrier obtained in Example 43 was caused to carry 1 wt. % of potassium in the same manner as in Example 1. It was then reacted with oxygen in an amount of 5 mole % of the potassium. Eighteen grams of the thus-prepared catalyst, 100 ml of heptane and 150 g of propylene were charged in an autoclave, in which they were reacted at 150° C. for 15 hours. As a result of an analysis, it was found that the conversion of propylene, the selectivity of 4-methyl-1-pentene and the activity of the catalyst were 12%, 91% and 0.067, respectively.

Comparative Example 10

The dimerization reaction of propylene was conducted under exactly the same conditions as in Example 44 except that the catalyst was not subjected to the oxygen-contacting treatment. As a result of an analysis, it was found that the conversion of propylene, the selectivity of 4-methyl-1-pentene and the activity of the catalyst were 8%, 85% and 0.044, respectively.

EXAMPLE 45

Fifteen grams of the catalyst precursor prepared as in Example 1 were charged, without any oxygen treatment, as a catalyst to an autoclave made of stainless steel and having a volume of 1 liter. On the other hand, 150 g of propylene in which 100 ppm by weight of oxygen had been dissolved under pressure was also charged in the autoclave. They were reacted at 160° C. for 4 hours. As a result, the cumulative amount of oxygen reacted with the catalyst was calculated to be 0.8 mole % after completion of the reaction.

As a result of an analysis conducted in the same manner as in Example 1, it was found that the conversion of propylene, the selectivity of 4-methylene-1-pentene and the activity of the catalyst were 36%, 92% and 0.900, respectively.

Comparative Example 11

The dimerization reaction of propylene was carried out in exactly the same manner as in Example 45 except that propylene free of oxygen (oxygen content < 1 ppm) was used as a reactant. As a result of an analysis, it was found that the conversion of propylene, the selectivity of 4-methylene-1-pentene and the activity of the catalyst were 26%, 89% and 0.650, respectively.

EXAMPLE 46

Sixteen grams of the catalyst precursor carrying sodium amide prepared as in Example 39 was charged in an autoclave having an internal volume of 1 liter, followed by further addition of 100 ml of n-heptane and 150.0 g of propylene containing 100 ppm by weight of oxygen dissolved therein. They were reacted at 160° C. for 6 hours. The cumulative amount of oxygen reacted with the catalyst in the above reaction was calculated to be 1.1 mole %. As a result of an analysis, it was found that the conversion of propylene, the selectivity of 4-methylene-1-pentene and the activity of the catalyst were 34%, 90% and 0.531, respectively.

One hundred fifty grams of propylene free of oxygen (oxygen content < 1 ppm) were added to the autoclave in which the catalyst was contained. The reaction was carried out again at 160° C. for 5 hours. As a result of an analysis, it was found that the conversion of propylene, the selectivity of 4-methylene-1-pentene and the activity of the catalyst were 36%, 90% and 0.675, respectively.

Comparative Example 12

Under the same conditions as those employed in Example 46 except that propylene did not contain oxygen, the catalyst precursor was treated for 6 hours. Then, the contents of the autoclave were post-treated in the same manner as in Example 1. Thereafter, the dimerization reaction of propylene was carried out in the autoclave, which contained the above-treated catalyst, under exactly the same conditions as those followed in Example 46. As a result of an analysis, it was found that the conversion of propylene, the selectivity of 4-methylene-1-pentene and the activity of the catalyst were 28%, 86% and 0.525, respectively.

EXAMPLE 47

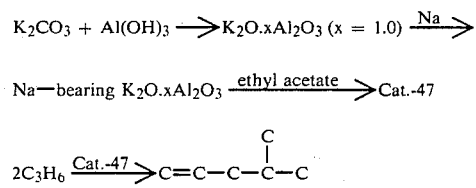

$$2C_3H_6 \xrightarrow{Cat.-47} C=C-C-\overset{\overset{\displaystyle C}{|}}{C}-C$$

A small amount of water was added to 138 g of anhydrous potassium carbonate and 156 g of aluminum hydroxide. The resulting mixture was kneaded thoroughly and then formed into pellets having a diameter of 1.6 mm and lengths of 5–8 mm through an extruder. The pellets were then placed in an alumina-made crucible and thereafter calcinated at 1000° C. for 5 hours in an air atmosphere, thereby obtaining a carrier. Sodium was added at 200° C. in a nitrogen atmosphere until the total amount of sodium had reached 10 wt. % of the whole weight of the carrier. Then, the temperature was raised to 400° C., at which the heating was continued for further 2 hours.

One hundred grams of the thus-prepared catalyst precursor were placed in a glass-made flask having a volume of 500 ml, followed by a further addition of 300 ml of n-heptane which contained 1.89 wt. % of ethyl acetate. The contents were stirred at 100° C. for 1 hours, thereby treating the catalyst with the ethyl acetate. The amount of ethyl acetate used for the treatment was 10 mole % of the sodium. Using the thus-obtained catalyst, the dimerization reaction of propylene was conducted by the fixed-bed continuous flow reaction method. Namely, while maintaining the reaction temperature and pressure at 150° C. and 90 kg/cm², respectively, the reaction was carried out by introducing propylene at a liquid hourly space velocity (LHSV) of 2.0 hr$^{-1}$. The conversion of propylene reached a steady level, 41%, in 20 hours. The content of 4-methyl-1-pentene in the reaction products was 93%. The reaction was allowed to proceed further. The half-life of the catalyst activity, namely, the time required until the conversion of propylene dropped from the maximum level to one half thereof, exceeded 1500 hours.

EXAMPLE 48

A catalyst was prepared following the procedures of Example 47 except that instead of the ethyl acetate treatment of the catalyst precursor with the n-heptane containing ethyl acetate, the catalyst precursor was treated with ethanol in an amount equivalent to 10 mole % of the carried sodium in the same manner as in Example 2. Using the thus-prepared catalyst, the dimerization reaction of propylene was carried out in the same manner as in Example 47. The conversion of propylene reached a steady level, 39%, in 20 hours. The content of 4-methyl-1-pentene in the reaction products was 93%. The reaction was allowed to proceed further. The half-life of the catalyst activity exceeded 1500 hours.

EXAMPLE 49

A catalyst was prepared following the procedures of Example 47 except that instead of the ethyl acetate treatment of the catalyst precursor with the n-heptane containing ethyl acetate, the catalyst precursor was treated with ethyl ether in an amount equivalent to 20 mole % of the carried sodium in the same manner as in Example 13. Using the thus-prepared catalyst, the dimerization reaction of propylene was carried out in the same manner as in Example 47. The conversion of propylene reached a steady level, 42%, in 20 hours. The content of 4-methyl-1-pentene in the reaction products was 92%. The reaction was allowed to proceed further. The half-life of the catalyst activity exceeded 1500 hours.

EXAMPLE 50

A catalyst was prepared following the procedures of Example 47 except that instead of the ethyl acetate treatment of the catalyst precursor with the n-heptane containing ethyl acetate, the catalyst precursor was treated with formaldehyde diethylacetal in an amount equivalent to 20 mole % of the carried sodium in the same manner as in Example 16. Using the thus-prepared catalyst, the dimerization reaction of propylene was carried out in the same manner as in Example 47. The conversion of propylene reached a steady level, 41%, in 20 hours. The content of 4-methyl-1-pentene in the reaction products was 92%. The reaction was allowed to proceed further. The half-life of the catalyst activity exceeded 1500 hours.

EXAMPLE 51

A catalyst was prepared following the procedures of Example 47 except that instead of the ethyl acetate treatment of the catalyst precursor with the n-heptane containing ethyl acetate, the catalyst precursor was treated with triethyl orthoacetate in an amount equivalent to 20 mole % of the carried sodium in the same manner as in Example 17. Using the thus-prepared catalyst, the dimerization reaction of propylene was carried out in the same manner as in Example 47. The conversion of propylene reached a steady level, 38%, in 20 hours. The content of 4-methyl-1-pentene in the reaction products was 92%. The reaction was allowed to proceed further. The half-life of the catalyst activity exceeded 1500 hours.

EXAMPLE 52

A catalyst was prepared in the same manner as in Example 47 except that instead of the ethyl acetate treatment of the catalyst precursor with the n-heptane containing ethyl acetate, the catalyst precursor was treated with oxygen in an amount equivalent to 2 mole % of the carried sodium in the same manner as in Example 1. Using the thus-obtained catalyst, the dimerization reaction of propylene was carried out in the same manner as in Example 47 except that propylene was introduced at LHSV of 1.4 hr$^{-1}$.

The conversion of propylene reached a steady level, 38%, in 20 hours. The content of 4-methyl-1-pentene in the reaction products was 93%. The reaction was allowed to proceed further. The half-life of the catalyst activity exceeded 1500 hours.

EXAMPLE 53

A continuous dimerization reaction of propylene was carried out in the same manner as in Example 47 except that the catalyst precursor was not treated with ethyl acetate. However, the propylene contained 19 ppm of oxygen and its LHSV was 1.0 hr$^{-1}$. After 80 hours, the conversion of propylene and the selectivity of 4-methyl 1-pentene were 46% and 89%, respectively. At this stage, the cumulative amount of oxygen reacted with the catalyst was 0.8 mole %. Even after 800 hours (at which, the cumulative amount of oxygen reacted with the catalyst was 8 mole %), the selectivity was still increasing little by little.

What is claimed is:

1. A process for preparing 4-methyl-1-pentene by the dimerization reaction of propylene in the presence of a catalyst being prepared by bringing a catalyst precursor in contact with at least one oxygen-containing compound selected from the group consisting of oxygen, alcohols containing 1 - 5 carbon atoms, ethers represented by the following formula (2):

$$R^1OR^2 \qquad (2)$$

wherein $R^1$ and $R^2$ mean individually a hydrocarbon residual group containing 1–5 carbon atoms, acetals represented by the following formula (3):

$$R^3-\underset{\underset{R^4}{|}}{\overset{\overset{OR^5}{|}}{C}}-OR^6 \qquad (3)$$

wherein $R^3$, $R^4$ and $R^5$ denote individually a hydrogen atom or a hydrocarbon residual group containing 1–5 carbon atoms and $R^6$ means a hydrocarbon residual group containing 1–5 carbon atoms, orthocarboxylates represented by the following formula (4):

$$R^7-\underset{\underset{OR^8}{|}}{\overset{\overset{OR^9}{|}}{C}}-OR^{10} \qquad (4)$$

wherein $R^7$ is a hydrogen atom or a hydrocarbon residual group containing 1–5 carbon atoms, and $R^8$, and $R^9$ and $R^{10}$ mean individually a hydrocarbon residual group containing 1–5 carbon atoms, and esters represented by the following formula (5):

$$R^{11}COOR^{12} \qquad (5)$$

wherein $R^{11}$ means a hydrogen atom or a chain or cyclic, aliphatic hydrocarbon residual group containing 1–15 carbon atoms or an aryl or aralkyl group containing 6–20 carbon atoms, and $R^{12}$ means a hydrocarbon residual group containing 1–5 carbon atoms; wherein the catalyst precursor consists of at least one element or compound selected from the group consisting of sodium, potassium, sodium amide and potassium amide supported on a carrier consisting principally of a compound represented by the following formula (1)

$$K_2O.xAl_2O_3 \qquad (1)$$

wherein x has a value in the range of $0.5 \leq x \leq 11$, wherein the catalyst precursor is optionally hydrogenated prior to the use thereof.

2. A process as claimed in claim 1, wherein the carrier is substantially formed of the compound represented by the formula (1) only.

3. A process as claimed in claim 1, wherein the carrier is formed of a mixture of the compound represented by the formula (1) and a small amount of potassium carbonate.

4. A process as claimed in claim 3, wherein the amount of potassium carbonate in the carrier is less than 30 wt. % of the compound represented by the formula (1).

5. A process as claimed in claim 2 or 3, wherein the amount of at least one element or compound selected from the group consisting of sodium, potassium, sodium amide and potassium amide supported on the carrier is 0.1–20 wt. % of the carrier in terms of elementary sodium and/or elementary potassium.

6. A process as claimed in claim 2 or 3, wherein the amount of oxygen used for the contacting treatment is within the range of from 0.1–20 mole % of the element or compound supported on the carrier.

7. A process as claimed in claim 2 or 3, wherein the amount of at least one oxygen-containing compound selected from the graph containing of the alcohol having 1–5 carbon atoms, ether represented by the formula (2), acetal represented by the formula (3), orthocarboxylate represented by the formula (4) or ester represented by the formula (5) used for the contacting treatment is within the range of 0.5–80 mole % of the element or compound supported on the carrier.

8. A process as claimed in claim 2 or 3, wherein the catalystprecursor optionally hdrogenated is brought into contact with oxygen and then with at least one oxygen-containing compound selected from the group consisting of alcohols having 1–5 carbon atoms, ethers represented by the general formula (2), acetals represented by the formula (3), orthocarboxylates represented by the formula (4), and esters represented by the formula (5).

9. A process as claimed in claim 2 or 3, wherein the catalyst precursor, optionally hydrogenated, is brought into contact with propylene and then with oxygen.

10. A process as claimed in claim 2 or 3, wherein the catalyst precursor, optionally hydrogenated, is brought into contact with oxygen, with propylene and then with oxygen.

11. A process as claimed in claim 2 or 3, wherein the hydrogen treatment is carried out at a temperature in the range of 150°–400° C., at a pressure up to 100 kg/cm$^2$, and for 0.5–10 hours.

12. A process as claimed in claim 1, wherein propylene is dimerized at a temperature in the range of 100°–250° C. and a pressure of 20–200 kg/cm$^2$ to prepare 4-methyl-1-pentene.

13. A process for preparing 4-methyl-1-pentene by the dimerization reaction of propylene in the presence of a catalyst consisting of at least one element or compound selected from the group consisting of sodium, potassium, sodium amide and potassium amide supported on a carrier consisting principally of a compound represented by the following formula (1):

$$K_2O \cdot xAl_2O_3 \quad (1)$$

wherein x has a value in the range of $0.5 \leq x \leq 11$, wherein the catalyst is optionally hydrogenated prior to the use thereof, wherein the process comprises employing as a reaction raw material propylene containing 2–500 ppm by weight of oxygen.

14. A process as claimed in claim 13, wherein the dimerization is effected by switching the oxygen-containing propylene to oxygen-free propylene when the cumulative amount of oxygen used for the contacting treatment of the catalyst has reached a level in the range of 0.1–20 mole % of the element or compound supported on the carrier.

* * * * *